United States Patent [19]

Snaith et al.

[11] Patent Number: 5,171,847

[45] Date of Patent: Dec. 15, 1992

[54] ALKALINE EARTH, TRANSITION AND LANTHANIDE METAL INORGANIC SALT COMPLEXES

[75] Inventors: Ronald Snaith; Dominic S. Wright; Alan T. Brooker; Simon R. Drake, all of Cambridge, Great Britain

[73] Assignee: The Associated Octel Company Limited, United Kingdom

[21] Appl. No.: 548,092

[22] Filed: Jul. 5, 1990

[30] Foreign Application Priority Data

Jul. 6, 1989 [GB] United Kingdom ............... 8915531

[51] Int. Cl.$^5$ ............... C07C 211/10; C07F 3/00; C07F 5/00; C07F 7/00; C07F 11/00; C07F 15/00; C07F 9/00; C07F 13/00; C07F 9/22; C07F 19/00; C07F 1/00; C07D 239/10
[52] U.S. Cl. .................................. 534/16; 556/1; 556/42; 556/45; 556/51; 556/57; 556/110; 556/118; 556/136; 556/138; 534/15; 260/665 R; 260/665 G
[58] Field of Search .............. 534/15, 16; 556/42, 556/45, 51, 57, 110, 118, 136, 138; 260/665 R, 665 G

[56] References Cited

U.S. PATENT DOCUMENTS 3,205,130 9/1965 Terry et al. ................. 514/89
5,045,244 9/1991 Marlett ...................... 556/118 X

FOREIGN PATENT DOCUMENTS 1261617 1/1972 United Kingdom.
1362699 8/1974 United Kingdom.
1418321 12/1975 United Kingdom.
1485791 9/1977 United Kingdom.
2211189 6/1989 United Kingdom.

OTHER PUBLICATIONS

Brini et al., *C. R. Acad. Sci. Paris, Ser. C.*, 268(23) 2040-1 (1969).
Eastmond et al., "Silylilation as Protective Method for Terminal Alkynes in Oxidative Couplings", *Tetrahedron* 28(17) 4601-16 (1972).
*Chemical Abstracts*, vol. 63, No. 13974a abstracting the above-identified U.S. Pat. No. 3,205,130.
Search Report dated Oct. 26, 1989, issued by the U.K. Patent Office.

*Primary Examiner*—Robert L. Stoll
*Assistant Examiner*—John M. Covert
*Attorney, Agent, or Firm*—Renner, Otto, Boisselle & Sklar

[57] ABSTRACT

Novel metallo-organic complexes of the formula $(M_xX_z.nL)y$ where M is an alkaline earth metal, a transition metal(at. Nos. 21-30, 39-48 and 72-80 inclusive) or a rare earth metal (at. Nos. 57-71 inclusive), X is an anion e.g. $Cl^-$, $Br^-$, $NO_3^-$, $NCS^-$ etc. and L is a Lewis base, are prepared by reacting a source of the metal M under anhydrous conditions with an anhydrous ammonium salt of the anion X in the presence of the Lewis base, and cooling the reaction mixture to precipitate the complex.

12 Claims, No Drawings

ALKALINE EARTH, TRANSITION AND LANTHANIDE METAL INORGANIC SALT COMPLEXES

This invention relates to organic complexes of inorganic metal salts of alkaline earth metals (i.e. metals of GpIIA of the Periodic Table), the metals having atomic numbers running from 21 (Sc) to 30 (Zn) inclusive, from 39 (Y) to 48 (Cd) inclusive and 72 (Hf) to 80 (Hg) inclusive, (referred to herein as the transition metals), and rare earth metals (i.e. metals having atomic numbers from 57 (La) to 71 (Lu) inclusive, referred to herein as metals of the lanthanide series.

In our published European application EP-A-0 317 087 there is disclosed a novel route for the preparation of organic complexes of inorganic metal salts of Gp.I metals, that is to say the alkali metals Li, Na, K, etc. Of particular interest and importance in that case are the lithium complexes, especially lithium halide complexes with electron donor ligands (Lewis bases) such as hexamethylphosphoramide (HMPA), tetramethylethylenediamine (TMEDA) and pentamethyldiethylenetriamine (PMDETA).

In general such inorganic metal salt complexes may be assigned the formula $(M_xX.nL)_y$, where M is the alkali metal, especially lithium, X is an anion, preferably $Cl^-$, $Br^-$, $I^-$, $SCN^-$, $BF_4^-$, $ClO_4^-$, $CO_3^{2-}$, and especially the halides or $SCN^-$, L is the Lewis base, x is the valency of the anion, usually 1 or 2, n is a number, usually 1, 2 or 4, and y is an integer up to infinity depending upon the degree of lattice formation by the complex.

In accordance with EP-A-0 317 087, such complexes are readily prepared by reacting the alkali metal, or an alkali metal hydride or alkyl, with an anhydrous ammonium salt of the anion X, the reaction being carried out under anhydrous conditions and under an inert atmosphere, in the presence of a hydrocarbon solvent, preferably an arene, and especially toluene, and in the presence of the ligand L. The reaction proceeds to completion quite readily at moderately elevated temperatures, e.g. 40° C. to 60° C., and the product complex is recovered quite easily, and usually in crystalline form, by cooling, e.g. refrigerating a solution of the reaction product. The reaction is accompanied by the vigorous evolution of gas, ammonia and hydrogen in the case of an elemental alkali metal reactant, or a hydride, and a mixture of ammonia and an alkane, e.g. in the case of the preferred n-butyl lithium reactant, n-butane.

Besides the ease of reaction and high yields which are attributable to the fact that the formation and evolution of ammonia and either hydrogen or alkane drives the reaction substantially to completion, a particular benefit of the reaction is that although anhydrous conditions and reagents are called for, these are not absolutely critical, and ordinary analar grade anhydrous starting materials can be used, and extreme steps to maintain substantially anhydrous conditions in the reaction zone need not be taken. This is in considerable contrast to the previously known procedures for the production of alkali metal salt complexes, e.g. alkali metal halide complexes and especially lithium halide complexes, involving, for example, dissolution of the alkali metal halide in the donor ligand, and which require the total exclusion of moisture from the reactants and the reaction zone, in order to avoid hydration problems in the final product. Extreme steps have therefore had to be taken to predry the reactants, and to exclude moisture from the reaction medium. Also, the extremely high lattice energy of some inorganic alkali metal salts such as lithium chloride make complete dissolution in the ligand almost impossible.

In accordance with the present invention, it has now been found that that technique can be applied to Gp.IIA metals, i.e. alkaline earth metals such as Mg, Ca, Sr, Ba; to metals of the lanthanide series, e.g. lanthanum and europium; and to transition metals e.g. yttrium, manganese and the others hereinbefore listed. Also it has been found that similar procedures can be used to prepare complexes containing two or more different alkaline earth, transition or lanthanide metals, including combinations of alkaline earth, transition and lanthanide metals, as well as complexes containing an alkaline earth, transition and/or lanthanide metal with either an ammonium ion or an alkali metal. These latter complexes, i.e. containing two or more metal (including ammonium) cations can either be prepared by using two or more different metal-containing reagents in the initial reaction, or by subsequent $NH_4^+$ substitution. Moreover, many of the complexes formed in accordance with the invention are believed to be novel compositions of matter.

The metallo-organic complexes produceable in accordance with this invention are of utility as intermediates in the manufacture of other alkaline earth metal, transition and lanthanide compounds particularly where solubility of the starting materials in organic solvents or a relatively low melting point is required. They also find utility as high purity electrolytes, lytes, for example in the electrolytic deposition and recovery of highly pure alkaline earth metals and lanthanide metals. They also show possible utility in the vapour phase deposition of lanthanide and other metal oxide films, as polymerisation initiators and possibly as antiknock additives in gasoline, especially the manganese complexes.

Whereas, and as in the method previously described in EP-A-0 317 087, the alkaline earth, transition or lanthanide metal containing reagent used in this invention for reaction with the ammonium salt in the presence of the donor ligand L, will be the elemental metal or a corresponding hydride, in some cases it may be preferred for solubility and reactivity reasons to use a Grignard type reagent, e.g. of the type RMgHal, where R is alkyl or alkenyl, e.g. methyl, ethyl or vinyl, and Hal is halide, especially chloride, bromide or iodide.

In accordance with a first aspect of the invention, therefore, there is provided a method for the preparation of inorganic metal salt complexes of metals of the alkaline earth, transition or lanthanide series, including complexes containing two or more different metals, which comprises reacting an alkaline earth, transition or lanthanide metal source (as hereinbefore defined), such source being either the elemental metal, a hydride of the metal in question, or in the case of magnesium a Grignard reagent, with an anhydrous ammonium salt, the reaction being carried out under anhydrous conditions and in a solvent, preferably a hydrocarbon such as toluene, containing an organic ligand L, preferably an electron donating organic ligand (Lewis base), and recovering the product formed from the reaction mixture.

More specifically, the invention provides a method for the preparation of metallo-organic complexes of the general formula:

$$(M_xX_z.nL)_y$$

where

M is a metal cation selected from alkaline earth metal cations, cations of metals having atomic numbers of from 21 to 30 inclusive, from 39 to 48 inclusive or 72 to 80 inclusive, and cations of rare earth metals having atomic numbers of from 57 to 71 inclusive; the metal cations M in the complex not necessarily all being the same, and with the proviso that the complex may contain a proportion of alkali metal or ammonium ($NH_4^+$) cations as the cations M;

x is the valency of the anion X;

X is an anion, all anions X not necessarily being the same;

z is the valency of the cation M, the values of x and z being adjusted in the case of complexes containing two or more different cations M and/or two or more different anions X to preserve the overall neutrality of the complex;

L is an organic, electron donating ligand;

n is a whole number; and y is a whole number having a value of from 1 to infinity, depending on the degree of network formation in the complex;

which comprises reacting a source of the metal M, or a mixture of such sources, including a mixture of a source of the metal M, with an alkali metal source, with an anhydrous ammonium salt, or a mixture of such salts, the reaction being carried out under anhydrous conditions in the presence of an organic solvent and in the presence of the organic electron donating ligand (L), and recovering the complex from the reaction mixture.

In accordance with a second aspect of the invention, there are provided inorganic metal salt complexes of the formula:

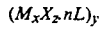

where M, X, L, x, z, n and y are as defined above.

As the ammonium salt there may be used an ammonium halide $Cl^-$, $Br^-$, $I^-$, thiocyanate ($NCS^-$), chlorate ($ClO_4^-$), nitrate ($NO_3^-$), tetrafluoroborate ($BF_4^-$), hexafluorophosphate ($PF_6^-$) or carbonate ($CO_3^{2-}$).

As the organic ligand L, any suitable organic electron donor (Lewis base) may be used, the preferred organic electron donors (Lewis bases) being HMPA, TMEDA, PMDETA and DMPU viz. the compound

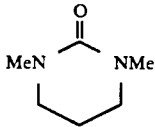

Other possible ligands are diethylether ($Et_2O$), 1,2-dimethyloxyethane (glyme), bis(2-methoxyethyl)ether (diglyme), dioxan and tetrahydrofuran. It is, however, to be understood that this listing is by no means exhaustive and other suitable organic ligands (Lewis bases) will suggest themselves to persons skilled in the art. The complexes of the invention will usually contain from 1 to 5 ligand molecules, i.e. the value of n will usually be 1, 2, 3, 4 or 5.

The reaction may be carried out in the absence of extraneous solvent using an excess of the electron donor L as the reaction medium. Preferably, however, the reaction medium is carried out in the presence of hydrocarbon solvent, especially an aromatic hydrocarbon, such as toluene.

Preferably the reaction will be carried out using stoichiometric amounts of the metal source, the ammonium salt and the liquid. However, excess ammonium salt may be used, as well as excess liquid which acts for example, as the reaction solvent. Excess ammonium salt gives rise to intermediate complexes containing a proportion of $NH_4^+$ cation which can be subjected to a cation replacement treatment to replace the $NH_4^+$ cation by other cations such as $Li^+$.

In some cases the reaction proceeds with considerable vigour even at room temperature, but in other cases reflux conditions are preferred. Ultrasound may be used to initiate reaction. Following the completion of the reaction, the product complex can be crystallised from solution by cooling to room temperature or below, for example by refrigeration. Alternatively before crystallisation, the product may be subjected to an $NH_4^+$ replacement treatment, to substitute, for example, a second metal cation in the lattice, e.g. the substitution of $NH_4^+$ in the lattice by $Li^+$ or by $Eu^{3+}$. Such substitution results from the formation of an intermediate metal/$NH_4^+$ complex, e.g. $Ba^{2+}$/$NH_4^+$, and in which the $NH_4^+$ can be replaced in the lattice by other metallic cations. As such other metallic cations there may be used not only cations of the alkaline earth, transition and lanthanide metals already mentioned, but others and especially alkali metal cations, e.g. $Na^+$, $K^+$ and $Li^+$.

Thus, according to another aspect of the invention, therefore, there is provided a method for the formation of alkaline earth, transition and lanthanide metal complexes as defined and wherein there is produced an intermediate product a complex comprising the reactant metal M, the anion $X^-$ corresponding to that of the ammonium salt, the ligand L, and the ammonium ($NH_4^+$) ion, and wherein the intermediate is subsequently treated with a source of a metal $M^1$, differing from the metal M, and including alkali metals as well as a different alkaline earth, transition or lanthanide metal, thereby to substitute the metal $M^1$ in the intermediate complex, in place of the ammonium ion.

In the alternative, two or more different metal sources may be used in the initial reaction, including, in this case, combinations of an alkaline earth, transition or lanthanide metal and an alkali metal source as described in EP-A-0 317 087, e.g. elemental alkali metal, or an alkali metal alkyl or hydride, giving rise directly to metallo-organic complexes containing two different metals.

In yet a further modification, it has been found that in the product complex ($M_xX_z.nLy$), the anion X corresponding to the anion of the anhydrous ammonium salt reactant can be replaced in a subsequent step by an alkyl (e.g. $CH_3^-$, $C_2H_5^-$ . . . etc) or alkoxy ($CH_3O^-$, $C_2H_5O^-$, $C_3H_7O^-$, n-butoxy etc.) group by reacting the complex with a metal, (e.g. alkali metal), alkyl or alkoxide. Thus the present invention provides a route to complexes of the type $(M_xR_z.nL)y$ and $(M_x(OR)_z.nL)y$ where M, L, x, y, z and n are as above defined and R is alkyl, e.g. lower alkyl of 1 to 6 carbon atoms.

In preparing alkaline earth, transition and lanthanide metal complexes according to the invention, the alkaline earth, transition or lanthanide metal source, including the alkali metal source, if present, and the ammonium salt are generally used in the stoichiometric proportions. Similarly the ligand L will be added in stoichiometric amounts, usually in molar quantities of 2, 3, 4 or 5 relative to the alkaline earth, transition or lanthanide metal source (including the alkali metal source if present).

Novel complexes according to this invention and methods of obtaining them are illustrated by the following examples.

EXAMPLE 1

La(NCS)$_3$.4HMPA

La metal (0.32 g, 2.3 mmol), solid ammonium thiocyanate (NH$_4$NCS) (0.56 g, 7.4 mmol), HMPA (1.2 ml, 6.7 mmol) were taken in toluene (10 ml), the mix treated with ultrasound for a short period, and then heated (at 50° C. for 24 hours, then at 90° C.). This initiated a reaction, gases being evolved and most of the solid dissolving. An extra 10 ml of toluene was added, and the mix filtered hot to give a colourless solution. Cooling afforded batches of colourless crystals.

Yield: over two batches 0.84 g, 49%.

m.pt.: plastic at about 120° C., melts 183° to 185° C.

Analysis: $C_{27}H_{72}LaN_{15}O_4P_4S_3$. Requires: C, 31.5; H, 7.0; N, 20.4; P 12.1%. Found: C, 31.6; H, 7.4; N, 20.4; P, 12.1%.

I.R., $^1H$ n.m.r. spectra: confirm presence of HMPA; sparingly soluble in toluene or benzene.

Crystal structure: discrete molecular complex, no intermolecular contacts, La 7-coordinate, with La-NCS contacts.

EXAMPLE 2

LaBr$_3$.4HMPA

La metal (0.35 g, 2.5 mmol), solid NH$_4$Br (0.74 g, 7.5 mmol), HMPA (1.3 ml, 7.5 mmol) were taken in toluene (20 ml). The mix was treated with ultrasound for 12 hours at 40° C., producing finely divided solids. It was then heated at 95° C. for 4 hours, when most solids reacted to give a colourless solution which was filtered. Cooling gave colourless cubic crystals.

Yield: 55% first batch.

m.pt.: plastic at about 165° C., melts 178° to 180° C.

Analysis: $C_{24}H_{72}Br_3LaN_{12}O_4P_4$. Requires: C, 26.3; H, 6.6; N, 15.3; Found: C, 26.2; H, 6.6; N, 14.9;

I.R., H n.m.r. spectra: confirm presence of HMPA; sparingly soluble in toluene or benzene.

Crystal structure: [La Br$_2$.4 HMPA]$^+$Br$^-$, i.e. La 6-coordinate within a complex cation; Br$^-$ counterions are dispersed in the lattice.

EXAMPLE 3

Following the same general procedure as Examples 1 and 2, lanthanum metal was reacted with three equivalents of anhydrous solid ammonium nitrate in the presence of toluene and three molar equivalents of HMPA.

The complex La(NO$_3$)$_3$.3HMPA is obtained in 76% yield, m.pt. 213° to 214° C.

X-ray analysis shows the complex to be monomeric, with bidentate NO$_3^-$, i.e. 9-coordinate La.

Yttrium and europium react in similar fashion with solid ammonium salts to form similar complexes.

For example, Y metal (5 mmol), NH$_4$NCS solid (15 mmol), HMPA (15 mmol) in toluene (10 ml) were treated with ultrasound for 1 hour, then refluxed at 110° C. for 12 hours. Over this period, all the solids reacted and dissolved. Cooling of the resulting solution gave crystals of Y(NCS)$_3$.3HMPA, yield 80%, m.pt. 177°–179° C. C, H, N, P analyses agree with this formulation.

Similar reactions employing Eu metal afforded the complexes Eu (NCS)$_3$.2TMEDA and Eu(NCS)$_3$.4DMPU* (m.pt. 127°–131° C.). The presence of Eu$^{3+}$ (rather than Eu$^{2+}$) in these complexes was established by cyclic voltametry and confirmed by crystallographic stands which confirm a nonomeric structure with 7-coordinates Eu$^{3+}$.

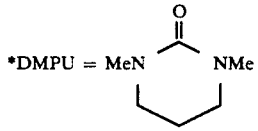

EXAMPLE 4

Following the same general procedure, i.e. by reacting solid alkaline earth metal (Ca, Ba, Sr) or CaH$_2$ and two molar equivalents of an anhydrous ammonium salt (NH$_4$X) in toluene containing 3 or 4 molar equivalents of the ligand L (HMPA) under reflux conditions for from 1 to 8 hours, the following halide complexes have been obtained, and their compositions confirmed by analysis.

| Complex | Yield % | m.pt. °C. |
|---|---|---|
| CaCl$_2$.3HMPA | 82 | 194–196 |
| CaBr$_2$.4HMPA | 76 | 220–225 |
| CaI$_2$.4HMPA | 80 | 115–119 |
| SrCl$_2$.3HMPA | 33 | 161–165 |
| SrBr$_2$.4HMPA | 93 | 127–130 |
| SrI$_2$.4HMPA | 86 | 193–196 |
| BaBr$_2$.4HMPA | 87 | 160–164 |
| BaI$_2$.4HMPA | 81 | 185–189 |

For magnesium halide complexes, Grignard reagents were used as the metal source. For example, reactions of Bu$^n$MgCl, and NH$_4$Cl (1:1 equivalents) with TMEDA (2 equivalents) and with HMPA (4 equivalents) proceeded, after 5 minutes heating, to give colourless solutions. On cooling, these afforded the complexes MgCl$_2$.2TMEDA (yield 49%, m.pt. decomp. 120° C. and MgCl$_2$.4HMPA (yield 67%, m.pt. 119°–121° C.), respectively. C, H, N, Cl analyses agree with these formulae.

Crystallographic studies of the above complexes indicate that SrI$_2$.4HMPA and BaBr$_2$.4HMPA are monomeric, octahedral with the halogen atoms trans. CaCl$_2$.3HMPA is ionic having a [(HMPA)$_3$Ca.($\mu$-Cl)$_3$.Ca(HMPA)]$^+$ cation and separated Cl$^-$ anion.

EXAMPLE 5

Following the same general procedure, i.e. reacting CaH$_2$ (solid) or Sr or Ba (metal) with solid ammonium thiocyanate (NH$_4$NCS) (two equivalents) in toluene containing HMPA (two or four equivalents), the following thiocyanate complexes have been prepared. Reaction is fast and vigorous. Elemental analysis conforms to the formulae assigned.

| Complex | Yield % | m.pt. °C. |
|---|---|---|
| Ca(NCS)$_2$.2HMPA | 50 | 99–102 |
| Ca(NCS)$_2$.4HMPA | 23 | 180–182 |
| Sr(NCS)$_2$.4HMPA | 77 | 174–175 |

-continued

| Complex | Yield % | m.pt. °C. |
|---|---|---|
| Ba(NCS)$_2$.4HMPA | 80 | 80–82 |

Crystallographic analysis indicates that Sr(NCS)$_2$.4HMPA is monomeric, octahedral with NCS$^-$ cis. Ca(NCS)$_2$.4HMPA and Ba(NCS)$_2$.4HMPA appear to be similar. Ca(NCS)$_2$.2HMPA appears to be polymeric on preliminary analysis.

In the reaction M:2NH$_4$NCS:2HMPA (M=Sr, Ba), an intermediate complex appears to result of the formula M(NH$_4$)$_2$(NCS)$_4$.4HMPA. Spectral analysis confirms the presence of NH$_4^+$ and elemental analysis corresponds. Deliberate doubling of the equivalents of NH$_4$NCS and HMPA, i.e. to a reactant molar ratio M:4NH$_4$NCS:4HMPA, produces the same intermediate: Ba(NH$_4$)$_2$(NCS)$_4$.4HMPA, yield 56%, m.pt. 91° to 93° C.

The reaction product with Sr is similar.

Crystallographic X-ray analysis shows Ba(NH$_4$)$_2$(NCS)$_4$.4HMPA to be an octahedral [Ba(NCS)$_4$.2HMPA]$^{2-}$ anion with 2NH$_4^+$ and 2HMPA in the lattice. The corresponding Sr complex is believed to be similar.

An equivalent complex is obtained using CaH$_2$ as the reactant. Thus the reaction of CaH$_2$(solid), NH$_4$NCS and HMPA in toluene at a molar ratio of 1:4:6, at 50° C. for two hours, produces on cooling and crystallisation a complex of the formula Ca(NH$_4$)$_2$(NCS)$_4$.4HMPA, yield 84%, m.pt. 133°–135° C.

EXAMPLE 6

By the reactions of solid alkaline earth metal (Sr, Ba) or alkaline earth metal hydride (CaH$_2$) with two equivalents of solid anhydrous ammonnium hexafluorophosphate (NH$_4$PF$_6$) or ammonium perchlorate (NH$_4$ClO$_4$) in toluene in the presence of 4 or 5 molar equivalents of HMPA at reflux temperature for about 1 hour, the following further complexes have been prepared.

| Complex | Yield % | m.pt. °C. |
|---|---|---|
| Ca(PF$_6$)$_2$.4HMPA | 72 | 160–162 |
| Sr(PF$_6$)$_2$.4HMPA | 73 | 220–222 |
| Ba(PF$_6$)$_2$.5HMPA | 75 | 172–175 |
| Ca(ClO$_4$)$_2$.4HMPA | 80 | 68–72 |
| Sr(ClO$_4$)$_2$.4HMPA | 73 | 173–176 |
| Ba(ClO$_4$)$_2$.4HMPA | 76 | 97–101 |

Elemental analysis and $^1$H n.m.r. agree with assigned formulae.

EXAMPLE 7

(a) Vinyl magnesium chloride (vinyl MgCl) in solution in toluene was reacted with two equivalents NH$_4$PF$_6$ in the presence of toluene and two molar equivalents of HMPA. The reaction mixture was exposed to ultrasound over a period of 45 minutes.

The complex MgCl(PF$_6$).2HMPA was obtained in 67% yield, m.pt. 272–274.

EXAMPLE 8

Solid alkaline earth metals (Sr, Ba) calcium hydride and butyl magnesium chloride were separately reacted with anhydrous solid ammonium nitrate in toluene in the presence of 4 molar equivalents of HMPA. In the case of butyl magnesium chloride, the reaction mixture was heated gently for 3 minutes. In the other cases, the reaction was performed under reflux conditions for 40 minutes (CaH$_2$), 1 hour (Sr), and 3 hours (Ba) respectively.

The following complexes were isolated:

| Complex | Yield % | m.pt. °C. |
|---|---|---|
| Mg(NO$_3$)$_2$.4HMPA | 66 | 119–122 |
| Ca(NO$_3$)$_2$.4HMPA | 84 | 132–134 |
| Sr(NO$_3$)$_2$.4HMPA | 87 | 117–120 |
| Ba(NO$_3$)$_2$.4HMPA | 92 | 136–138 |

Elemental analysis and $^1$H n.m.r. agree with assigned formulae.

EXAMPLE 9

The intermediate complex Ba(NH$_4$)$_2$(NCS)$_4$.4HMPA (alternatively expressed as [Ba(NCS)$_4$.2HMPA]$^{2-}$(NH$_4^+$)$_2$.2HMPA) obtained as in Example 5, reacts vigorously at room temperature in toluene with n-butyl lithium, and with europium, and additional HMPA with vigorous evolution of NH$_3$ to yield metal complexes of the formula Ba$_x$(Li or Eu)$_y$(NCS)$_z$.nHMPA. The exact values of x, y, z and n and the exact structure of the complex are still to be ascertained.

EXAMPLE 10

The complexes SrI$_2$.4HMPA, BaBr$_2$.4HMPA and LaBr$_3$.4HMPA undergo reaction with alkali metal alkyls, e.g. PhCH$_2$K, and with alkali metal alkoxides, e.g. potassium butoxide (n-BuOK) to yield complexes of the type [M(R)$_{2\,or\,3}$.nL]$_y$ and [M(OR)$_{2\,or\,3}$.nL]$_y$, respectively where M, L, and R are alkyl, n and y are as previously defined.

Specifically, lanthanide complexes of the type [LaBr$_3$.nL]$_y$, prepared for Example 2, viz the complex LaBr$_3$.4HMPA, reacts with lithium alkoxide (LiOR, where R is alkyl, e.g. n-butyl) to provide a lanthanum alkoxide complex of the formula La(OR)$_3$.4HMPA.

EXAMPLE 11

Further metal complexes according to the invention have been prepared as follows:

a) by co-reacting Ba and Li with NH$_4$SCN and HMPA in toluene at 80° C. for 4 hours. During this period the solid reactants dissolve, and cooling of the reactant solution at the end of 4 hours precipitates a mixed metal complex having a melting point of 66°–69° C. and shown to contain both metals. The provisional formula assigned to the complex is Ba$_x$Li$_y$ (NCS)$_z$.n HMPA, the stoichiometric proportion of which, i.e. the values of x, y, z, and n are still to be determined, as also is the exact crystallographic structure.

b) Sr and Ba metal were coreacted with NH$_4$ NO$_3$ and HMPA at a molar equivalent ratio of 1:1:4:8 in toluene at reflux temperature until the metals were dissolved. Cooling the solution precipitates a mixed metal complex analysing as Sr Ba (NO$_3$)$_4$.8HMPA, m.pt. 100°–103° C. in 77% yield.

c) Sr metal and Mg(ClO$_4$)$_2$ were coreacted with NH$_4$ClO$_4$ and HMPA (molar equivalents 1:1:2:8) in toluene at reflux temperature. Following dissolution of all solids the reaction solution is cooled to precipitate a product analysing as Mg Sr (ClO$_4$)$_4$.8HMPA in 65% yield.

EXAMPLE 12

Manganese metal (5 mmol), solid NH$_4$Br (15 mmol), and DMPU (15 mmol) were taken in toluene solvent, then treated with ultrasound for 1 hour at 40° C. The mix was heated for 12 hours at 80° C., this giving a brown-green solution. After filtration to remove a small amount of unreacted metal, standing at room temperature for two days gave a batch of light green crystals.

Yield: first batch, 92%
m.pt.: 125°-127° C.

C, H, N, Br analyses agree with the formula MnBr$_2$.2DMPU (Calc., 30.6, 5.1, 11.9, 34.0; Found, 31.5, 5.3 12.3, 33.3%, respectively).

$^1$H n.m.r.: DMPU signals present, broadened due to paramagnetic Mn$^{2+}$.

EXAMPLE 13

Mn metal (flake, 5 mmol), NH$_4$Cl (10 mmol) and excess HMPA were heated at 130° C. for 8 hours with continuous stirring. The reaction mixture was then filtered and the filtrate treated with a toluene/hexane mixture (1:1) to precipitate a white solid. On gentle warming the solid dissolved and on slow cooling recrystallised to give pale yellow cubic crystals, m.pt. 103°-105° C., yield 80%. C, H, N, P and Mn analysis corresponds to the formula MnCl$_2$.2HMPA.

EXAMPLE 14

Mn metal (powder, 5 mmol), NH$_4$Br (10 mmol) and HMPA (80 mmol) were heated in toluene to 50° C. and held at that temperature overnight. Following the evolution of gas from the reaction mixture, a pale green solution developed. This was filtered and refrigerated to give a light green crystalline product, m.pt. 85°-86° C., yield 81%. C, H, N, P and Mn analysis corresponds to the formula MnBr$_2$.2HMPA.

Repeat of the above procedure using NH$_4$I in place of NH$_4$Br gave a crystalline product, m.pt. 150°-152° C., yield 89%, C, H, N, P and Mn analysis corresponding to the formula MnI$_2$.2HMPA.

We claim:

1. A method for the preparation of metallo-organic complexes of the general formula:

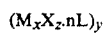

$(M_xX_z.nL)_y$ where

M is a metal cation selected from alkaline earth metal cations, cations of metals having atomic numbers of from 21 to 30 inclusive, from 39 to 48 inclusive or from 72 to 80 inclusive, and cations of rare earth metals having atomic numbers of from 57 to 71 inclusive; the metal cations M in the complex not necessarily all being the same, and with the proviso that in the complex may contain a proportion of alkali metal or ammonium (NH$_4^+$) cations as the cations M;

x is the valency of the anion X;

X is an anion, all anions X not necessarily being the same;

z is the valency of the cation M, the values of x and z being adjusted in the case of complexes containing two or more different cations M and/or two or more different anions X to preserve the overall neutrality of the complex;

L is an organic, electron donating ligand (Lewis base);

n is a whole number; and y is a whole number having a value of from 1 to a value approaching infinity, depending on the degree of network formation in the complex, which comprises reacting a source of the metal M, or a mixture of such sources, including a mixture of a source of the metal M with an alkali metal source, with a solid anhydrous ammonium salt, or a mixture of such salts, the reaction being carried out under anhydrous conditions in the presence of a hydrocarbon solvent and in the presence of the organic electron donating ligand (Lewis base), and recovering the complex from the reaction mixture.

2. A method according to claim 1, wherein the ligand is HMPA, PMDETA, TMEDA or DMPU.

3. A method according to claim 1, wherein the source of the metal(s) M is the elemental metal or a hydride.

4. A method according to claim 1, wherein the metal source is selected from Mg, Ca, Sr, Ba, La, Eu, Y and Mn.

5. A method according to claim 1, wherein the metal M is or comprises magnesium and the source of that metal is a magnesium Grignard reagent.

6. A method according to claim 1, wherein the ammonium salt is selected from ammonium halides (Cl$^-$, Br$^-$, I$^-$), nitrates (NO$_3^-$), carbonates (CO$_3^{2-}$), hexafluorophosphates (PF$_6^-$), chlorates (ClO$_4^-$), thiocyanates (NCS$^-$) and tetrafluoroborates (BF$_4^-$).

7. A method according to claim 1, wherein the solvent is an aromatic hydrocarbon.

8. A method according to claim 7, wherein the solvent is toluene.

9. A method according to claim 1, wherein the source of the metal M includes an alkali metal source.

10. A method according to claim 1, wherein there is recovered from the reaction mixture an intermediate product comprising product cations of the reactant metal M, the anion X$^-$ corresponding to that of the ammonium salt, the ligand L, and the ammonium (NH$_4^+$) ion, and wherein in a subsequent reaction the intermediate is treated with a source of cations of a metal M$^1$, different from those of metal M, thereby to substitute cations of the metal M$^1$ in place of the ammonium ions, and recovering the substituted product.

11. A method according to claim 10, wherein the intermediate product is treated to substitute the ammonium ions therein by alkali metal cations.

12. A method according to claim 1, wherein the product complex containing the anion X corresponding to that of the ammonium salt is reacted in a subsequent step with a metal alkyl or alkoxide thereby at least partially to replace the anion X in the complex with an alkyl or alkoxy group.

* * * * *